US006991532B2

(12) United States Patent
Goldsmith

(10) Patent No.: US 6,991,532 B2
(45) Date of Patent: Jan. 31, 2006

(54) METHOD AND APPARATUS FOR DECONTAMINATION FOR AUTOMOTIVE HVAC SYSTEMS

(75) Inventor: Samuel W. Goldsmith, Waterford, MI (US)

(73) Assignee: Valeo Climate Control Corp., Auburn Hills, MI (US)

(*) Notice: Subject to any disclaimer, the term of this patent is extended or adjusted under 35 U.S.C. 154(b) by 0 days.

(21) Appl. No.: 11/008,695

(22) Filed: Dec. 9, 2004

(65) Prior Publication Data
US 2005/0124286 A1 Jun. 9, 2005

Related U.S. Application Data

(63) Continuation-in-part of application No. 10/731,562, filed on Dec. 9, 2003, now abandoned.

(51) Int. Cl.
F24F 7/00 (2006.01)
(52) U.S. Cl. .................. 454/156; 454/157; 454/75; 422/28; 422/186.07; 210/760
(58) Field of Classification Search ................ 454/156, 454/75, 229, 239, 256, 157; 422/105, 116, 422/120, 121, 186.07, 3, 4, 28; 210/758, 210/760; 236/49.3
See application file for complete search history.

(56) References Cited

U.S. PATENT DOCUMENTS

| 3,750,556 | A | 8/1973 | Duke et al. |
| 4,451,435 | A | 5/1984 | Holter et al. |
| 4,658,707 | A | 4/1987 | Hawkins et al. |
| 5,648,046 | A | 7/1997 | Weibel |
| 5,762,665 | A | 6/1998 | Abrahamian et al. |
| 5,788,930 | A | 8/1998 | McMurray |
| 5,810,896 | A | 9/1998 | Clemens |
| 5,820,828 | A | 10/1998 | Ferone |
| 5,938,523 | A | 8/1999 | Khelifa et al. |
| 5,942,026 | A | 8/1999 | Erlichman et al. |
| 6,432,367 | B1 | 8/2002 | Munk |
| 6,773,477 | B2 | 8/2004 | Lindsay |
| 2002/0176809 | A1 | 11/2002 | Siess |
| 2003/0091363 | A1 | 5/2003 | Hoffman et al. |
| 2004/0047776 | A1 | 3/2004 | Thomsen |
| 2004/0120845 | A1 | 6/2004 | Potember et al. |
| 2004/0262240 | A1 * | 12/2004 | Oke .......................... 210/758 |

* cited by examiner

Primary Examiner—Jiping Lu
(74) Attorney, Agent, or Firm—Ronald Courtney

(57) ABSTRACT

A method and apparatus for passenger vehicles, including light and heavy truck, heating, ventilation and air conditioning systems, particularly HVAC systems, using oxidants to reduce contaminants and increase passenger comfort levels in such vehicles.

5 Claims, 8 Drawing Sheets

METHOD AND APPARATUS FOR DECONTAMINATION FOR AUTOMOTIVE HVAC SYSTEMS

This application is a continuation in part of application Ser. No. 10/731,562 filed Dec. 9, 2003 abandoned.

FIELD OF INVENTION

This invention relates to the field of passenger vehicles, including light and heavy truck, heating, ventilation and air conditioning systems, particularly HVAC systems, using oxidants as means to reduce contaminants and increase passenger comfort levels in such vehicles.

BACKGROUND OF THE INVENTION

Air treatment systems, such as heating, ventilation and air conditioning systems, perform three principal functions in automotive vehicle applications: heating, cooling and dehumidifying the air inside the vehicle. Air thusly treated leads to more even temperature and humidity control, thereby resulting in treated air for passengers to achieve a good level of passenger comfort. Distribution of air, transfer of heat, condensation of water, and maintenance of a closed (air and water tight) system are the steps used to meet these desired effects.

Current HVAC systems for automotive vehicles suffer numerous problems as it relates to ancillary effects of the primary heating, cooling and dehumidifying activities.

One of the chief deficiencies associated with current HVAC functional requirements is the promotion of bacteria, yeast, and fungal growth or development by promoting the ingestion, incubation, and even the continuous distribution of micro-organisms and derived products within the HVAC system and vehicle interior. Contamination of the HVAC system is inevitable, even with the use of filters. The value of filter function is lost when micro-organisms pass through the filter media. The offending organisms include, for example: *alternaria alternata, penicillium cyclopium, trichoderma harzianum, bacillus subtilis, bacillus licheniformis, bacillus cereus, acinobacter calcoaceticus, pseudomonas fluorescens, proteus hauseri, staphyloccus epidermis*, which generally are too small in size and too prevalent to employ traditionally economical solutions or methods to avoid their entry or distribution to or within the HVAC system.

HVAC systems often are described as working in fresh air or 'recirculation' modes. In both fresh air and recirculation mode, micro-organisms are drawn into the HVAC unit. Contamination of the HVAC unit components, including interior surfaces and duct work, necessarily takes place on a continuous basis because the air to be circulated and/or the circulated air is not sterile. Heat transfer, combined with the condensation of water, provides an environment perfectly suited for organism growth. Engine coolant, circulating through most vehicle heater cores while the engine is running, also transfers heat through the core providing a source of warmth. The presence of water vapor, in the form of relative humidity or condensate carryover, for example, can lead to an HVAC functional environment where maintenance, development and/or the growth of micro-organisms, (as well as a medium for such maintenance, development or growth) is created and even propagated. These conditions are, additionally, being maintained in a system that is generally as air and water tight as possible, with, preferably, only the intended entry and exit open. The HVAC functional environment is, therefore, basically a 'closed' system that will not function at an optional level if other openings are added (or interruptions are made) along the air flow surface.

U.S. Pat. No. 5,788,930 issued in Aug. 4, 1998, McMurray 'Apparatus for Purifying an Environment Using Ozone Generation', addresses the issue of safe and efficient purification of an enclosure, including buildings or vehicles" but does not anticipate the functional requirements of vehicle HVAC systems, and focuses on "efficient purification" in the control of ozone concentrations.

U.S. Pat. No. 5,648,046 issued in Jul. 15, 1997, Weibel 'Method and System For disinfecting Air In Air Conditioning Ducts,' describes a method for disinfecting air in ventilation ducts by the use and application of a vaporized ammonia solution that is ionized and distributed within a set of grounded duct work; ionized vapor migrates to the interior walls of the duct due to the 'grounding effect', thereby reducing bacteria and mold growth by utilizing the bactericidal properties of ammonia. This reference does not disclose, suggest or anticipate such an application within a vehicle HVAC system.

U.S. Pat. No. 3,750,556 issued in Aug. 7, 1973, Douglas Roy Duke et al 'Air Purifying Means,' relates to an "apparatus for conditioning the air being circulated through a confined space". It does not disclose, suggest or anticipate the HVAC system as a primary source of contamination and would be an ineffective means of addressing the herein described HVAC specific problems, such as the growth or development ('contamination') of microorganisms on an evaporator.

U.S. Pat. No. 5,810,896 issued Sep. 22, 1998, Clemens, 'Air filtration and purification system for vehicle,' discloses an air filtration and purification system for the interior of a closed vehicle, more particularly, a system mounted in the interior of a closed vehicle wherein pollutants are prevented from influxing from outside the vehicle.

U.S. Pat. No. 5,938,523 issued Aug. 17, 1999, Khelifa et al, 'Device for removing the noxious and aromatic substance from an air flow fed into the interior of a vehicle,' discloses an absorbent containing device to absorb noxious and aromatic matter.

U.S. Pat. No. 5,942,026 issued Aug. 24, 1999, Erlichman et al, 'Ozone generators useful in automobiles,' described inlet air ionization structures useful to produce ozone of the inlet of an internal combustion engine. Column 3 describes ozone in the interior of the filter housing, and that ozone assists in flame propagation inside the combustion chamber.

U.S. Pat. No. 5,762,665 issued Jun. 9, 1998, Abrahamian et al, 'Vehicular air purification system,' discloses a vehicle air purification system having specific outlet vents. In column 5, its plurality of components include active and passive filter units.

U.S. Pat. 4,658,707 issued Apr. 21, 1987, Hawkins et al, 'Automatic air purifier for vehicles' describes an air purifier which can be positioned within various places in a confined space such as a vehicle interior where smoke may be present' to purify the air therein. It further describes an air filter for filtering tobacco smoke and other airborne impurities.

U.S. patent Publication 2002/0176809 A1, Siess, Nov. 28, 2002, describes a method and apparatus for securing the comfort and health of human beings by the production and maintenance of conditioned air, with, for example, as shown in FIG. 1 of Siess, an air handling device such as those used to condition transportation vehicles that can 'clean' air to the cargo holds of a locomotive box car, light and heavy duty delivery trucks and other commercial vehicles, and describes that a similar concept could be used in the ventilation system for conditioning of the air throughout a building or wherein airborne pollutants are generated, such as, but not limited to, copier rooms, computer rooms, bathrooms, operating rooms or zones or rooms having a legislatively mandated level of high air purity. It, therefore, does not anticipate the level of air purification and not just cleaning or filtering, required in a true passenger inhabited space of a passenger vehicle, and, in fact, since it is a filtering system, suggests that its concept is fit even for retrofitting into an existing ventilation systems to clean the air, not the HVAC unit. It also describes no regulation of oxidant levels in an HVAC temperature control chamber, and does not include an oxidant sensor in the passenger compartment.

The Siess disclosure involves a chemical reaction taking place in the encapsulation chamber while the passenger is in the vehicle. There appears to be no amount of component rearrangement, control means, sensor, timer or switch additions that can be made to allow this reaction to occur outside the encapsulation chamber during vehicle operation with a human or animal occupying space in the passenger compartment. In addition, the goal of Siess appears to require the movement of polluted outside air through the device into the passenger environment, thereby not addressing the need for dealing with contaminated air when operating in recirculation mode.

U.S. Pat. No. 5,820,828, Ferone, Oct. 13, 1998, describes a modular ozone distributing system for producing and distributing ozone to an air duct network of a building.

Neither Siess nor Ferone have foreseen the problem or solution of the HVAC system itself as being a primary or secondary source of air pollution. Therefore, the inlet appears to effect on a stream of air and move the stream into a space outside of the unit. The present invention is intended to impact the space within the unit itself, and, unlike the prior art, allows for selective operation when a passenger is not in the vehicle.

SUMMARY OF THE INVENTION

As stated above, the present invention, unlike many prior art air conditioning systems, is not an air cleaner or air purifier, but provides a means for flushing or decontaminating an passenger vehicle HVAC system by means of applying an oxidant, preferably ozone, to the micro-organisms that exist on the interior surfaces of an HVAC system, including, but not limited to, the interior HVAC housing walls and interior duct surfaces, and components interior to the HVAC such as, but not limited to, the unit heat exchangers, doors, links, resistor(s), and power module(s). Preferably, the oxidant is applied in a manner so as to perfuse or completely stay, for a period of time, in a region of or upon all exposed external surfaces of the heat exchangers, more preferably, upon all exposed external surfaces of the evaporator of the HVAC unit. Preferably, the oxidant surrounding as completely as possible (envelops) the surfaces where micro-organisms may occur.

In the present invention there is no need to clean or remove particulates or other matter from the outside fresh air or recirculated vehicle interior air that is, in traditional systems, drawn into the HVAC unit. A number of systems claim to provide a means of providing cleaner, more breathable air to the occupants of passenger vehicles by treating, using a variety of means, the fresh air that is drawn into the HVAC unit and subsequently delivered to the occupants of the vehicle. The present invention provides for improvement in the quality of breathable air as a result of or 'byproduct' of the disinfection or 'decontamination' process that is described herein.

The present invention relates to a means for providing for increased passenger comfort in an automobile vehicle, and, in particular, the automobile passenger compartment. Though the prior art often tries to filter or remove suspended matter from outside air as it comes into the interior environment, the present invention provides an increased level of passenger comfort by providing a means for addressing the prior art problem of elements in the HVAC unit, and, particularly, on HVAC unit elements such as the evaporator, causing conditions that lead to an HVAC functional environment that creates a breeding ground for bacteria, yeast, mold and fungal growth, and the like. The growth of micro-organisms significantly impacts passenger comfort due to contaminating allergens and odors. Oxidants, and preferably, ozone is employed, within the HVAC system, thereby controlling formation, growth, and development of micro-organisms. In preferred embodiments of the present invention, an oxidant sensor for detecting levels of oxidant, and, preferably, ozone, is located in the passenger compartment of the vehicle.

The present invention, therefore, further provides a non-filtering method to control contaminants related to microbiological growth, development or maintenance and associated allergens related thereto in an HVAC functional environment, thereby reducing odors and promoting passenger comfort in a way not done in the prior art.

Particularly, the present invention provides a means to prohibit, inhibit or reduce bacteria, yeast, mold and/or fungal growth, development or maintenance, within or associated with the HVAC system, thereby controlling formation, growth and/or concentration of odors and, in particular, 'off' or 'offensive' odors or allergens which might accompany such micro-organisms or related substances. Preferably ozone is employed, within the HVAC system, and more preferably, within the HVAC unit, as the principal element to control the formation, growth, development or maintenance of micro-organisms that leads to undesirable odor or allergen substances. The present invention, therefore, provides a means for oxidant, and, preferably, ozone generation integrated within the HVAC system, thereby taking advantage of the 'closed' characteristics of the system. This allows for the oxidant to be delivered directly to the contaminated components and surfaces. In addition, the present invention allows for the vehicle manufacturer to specify the oxidant concentration, time of delivery, and duration of exposure within the limits described herein below and, preferably, to best meet both performance and packaging requirements by providing multiple locations for oxidant generator placement.

The present invention further provides an decontamination system comprising an HVAC system having an HVAC unit, at least one ozone generator, at least one sensor means for detection of ozone levels, and at least one control means for regulating ozone levels in the HVAC unit.

As used herein, a generator is an apparatus by which an oxidant, preferably ozone is produced. A generator means, could, therefore, without limitation, be used to manufacture an oxidant, preferably ozone, for example by coronal discharge. Examples of companies manufacturing such means are: Lenntech Water& Luchtbeh Holding .v. Netherlands, Golden Electronics Technologies Co. ltd; Ez-Com System Inc; OZo Max Ltd and Air Zone®.

A sensor or sensor is any of the series of detection mechanisms used to monitor specified environment or conditions of the vehicle.

A sensor mean, could, therefore, without limitation, be a device located within the passenger cabin below the instrument panel, against the bulkhead. It can be, for example, a simple monitoring device that detects the oxidant level, preferably ozone, in preferred embodiments of the present invention, and communicates with the controller. Examples of manufacturing companies are: Ozone Lab Instruments; Applied Ozone Systems; Geneq Inc.

A controller is a mechanism by which multiples devices, such as generator, sensor, switches, and associated parts are regulated.

A controller means, could, therefore, without limitation, be programmable body controller like those present in all current passenger vehicles. They are programmed to monitor and control a variety of functions including other vehicle functions such as ignition, antilock brake sytems, safety systems such as seatbelt use, airbag inflation and seat occupancy.

Switches are control mechanisms, often for turning off or on access to processes or flows, for example, stopping or starting the ozone flow into an HVAC unit.

The present invention achieves a 'decontamination', (killing or inhibition of organism growth) on the surfaces and interior components of the HVAC system, and, especially, components, such as heat exchangers, of the HVAC unit, by creating an environment that is harmless to humans but septicidal, (bactericidal, bacteristatic, fungicidal or static, etc, or the like) for micro-organisms including bacteria, molds, yeast, fungi and the like. Traditional air treatment systems are drawn to methods for treating the fresh air that is drawn into the HVAC unit and delivered to the vehicle occupants. Some of these teach the application of chemicals, biocides or other substances which adhere to the interior of the HVAC system, thereby reducing the growth of micro-organisms. Such chemicals or biocides are often able to get into the passenger compartment or accumulate over time and come in contact with the vehicle occupant(s), thereby possibly exposing the occupant(s) to dangerous elements.

This present invention, unlike the above prior art, does not teach the application of chemicals, biocides or other means that adhere to the interior surfaces of an HVAC system or remain reactive during times when the vehicle is occupied by humans or animals. The present invention, by providing a means of disinfecting the interior of an HVAC system by the application of an oxidant, preferably ozone, leads to a system wherein the oxidant, preferably ozone, does not accumulate over time, nor does it remain adhered to surfaces. The present invention, therefore, presents the advantage that vehicle occupants are not in danger of being exposed to an accumulation of dangerous substances.

The present invention further preferably provides for the aspect of a feedback loop mechanism to sense oxidant concentration in the cockpit or passenger compartment of a motor vehicle, and the HVAC unit. By placing an oxidant sensor means, and, preferably, an ozone sensor in the cockpit or passenger compartment, preferably at a low level in the passenger compartment, at ozone levels deemed too high or otherwise unacceptable, ozone would cease to be generated, derived, transported or otherwise received into the HVAC unit. By low level is meant at a lower level of the cockpit or passenger compartment relative to the horizontal mid plane of the cockpit or passenger compartment, and at a level where any ozone, if present, would be rapidly detectable. Low level, as it relates to the passenger is preferably, at the level of the seat or below of the cockpit or passenger compartment, most preferably near or below foot level of the cockpit or passenger compartment, most preferably on a level in line with the level of the accelerator pedal or below on a standard vehicle. Decontamination would cease until ozone levels were again at an acceptable level in the cockpit or passenger compartment. This control preferably is achieved via a feedback mechanism involving, at a minimum, the generator and the sensor described herein. The present invention as described herein can be used at all times, as long as the level of ozone in the cockpit or passenger compartment does not rise to unacceptable levels. Preferably, the method of preferred aspects of the present invention are operated when there are no passengers within the cockpit or passenger compartment of the motor vehicle.

It is clear that the prior art addresses many issues related to the environmental problem of so-called 'in-door' air pollution. However none of the art cited above directly addresses or even appreciates or fully comprehends the root problem with respect to vehicle HVAC systems, that of a "functionally driven contamination". Air purification is the focus of these other inventions, not issues such as disinfection, asepsis, decontamination and the like or other controls of contaminants within the HVAC unit or in the HVAC functional environment or system.

The present invention, unlike many prior art systems, operates when the vehicle is not occupied (or needs to be controlled to pause or shut off when the vehicle is occupied), thereby providing passenger protections during operation. Preferably passenger protections are provided by a combination of monitoring and switching functions which are managed by the controller. The controller 10 is in communication with ignition switch 11, vehicle battery 16, control head 19, door ajar sensor 15, in all vehicles today. This invention adds monitoring of the oxidant, generator 1, switch 14, timer 18, fan 21 and doors 8, 7 to the controller 10 functions. Passengers protections are insured by monitoring vehicle entry, engine usage, oxidant level sensing and timing of oxidant generation. The present invention, in its preferred embodiments, also provides for monitoring of oxidant in the passenger compartment to protect passengers from exposure to the oxidant. Even more preferred embodiments of the present invention, monitor, for example, the door ajar switches, ignition and control heads and provide for stoppage of functioning of the oxidant generator or other components when activated by the presence of passenger in the motor vehicle. If these are operated by the passenger then the system is turned off. The air propulsion source or the 'blower' is located upstream of the heat exchangers in preferred embodiments of the present invention, creating a push-through system.

DETAILED DESCRIPTION OF THE INVENTION

Figure 1:
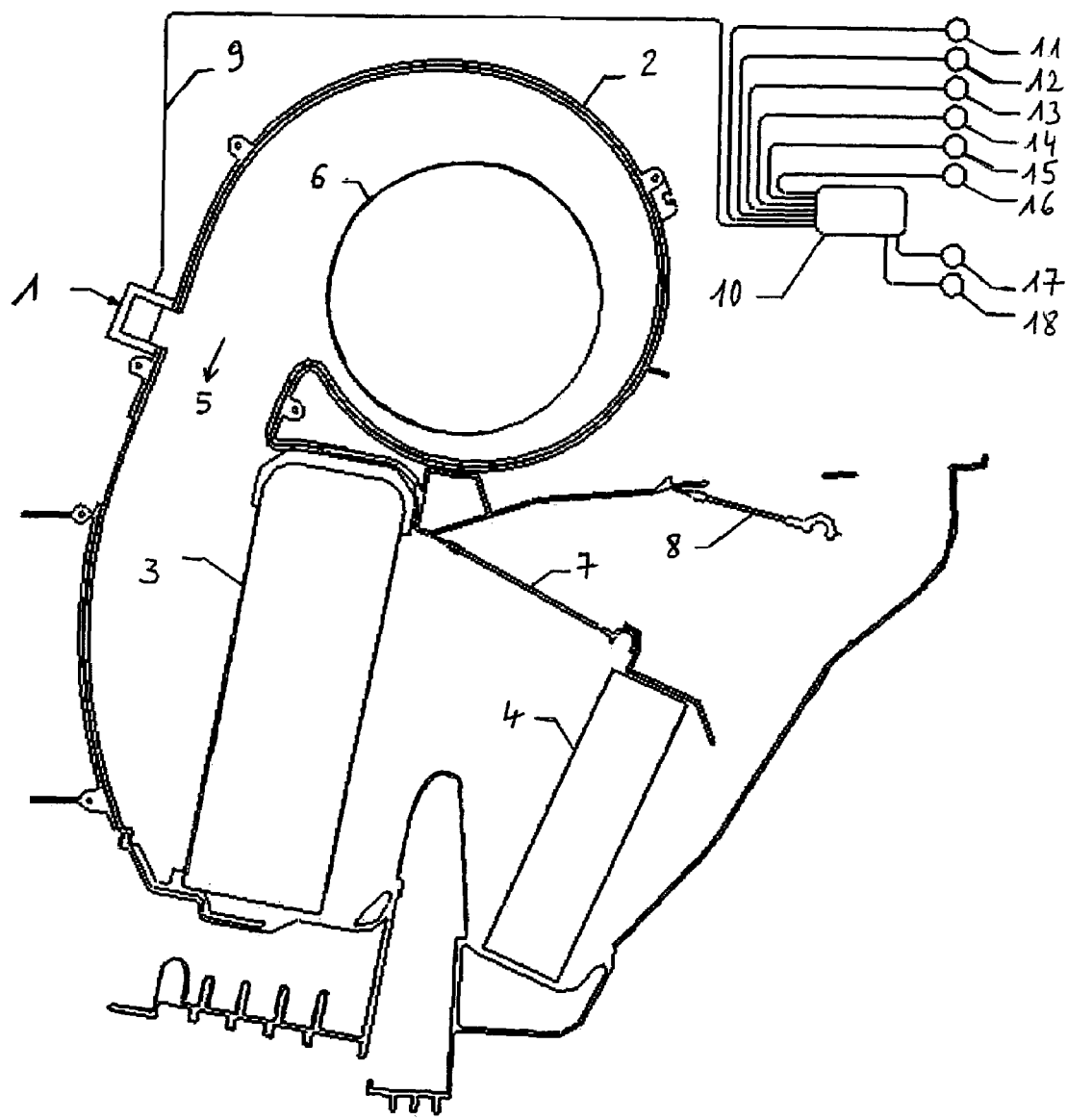
FIG. 1 is elevational cross-section view of an HVAC unit in accordance with an aspect of the present invention.

While prior art describes the terms "efficient purification" or air purification, the present invention focuses on the distribution of the oxidant within the vehicle, the distribution problem to be solved. In one aspect of the present invention, the timing of the generator operation and ozone generator design provide the necessary controls to prevent "over ozonation".

The molded materials, and, in particular, the plastic and plastic like materials from which an HVAC unit and ducts of the HVAC system are, preferably, made, cannot be sufficiently grounded for the interior surfaces to attract disinfection means such as ionized vapor to purport a solution. Water vapor, as a conductive medium, potentially causes electrical shorts to occur in several components of the HVAC unit, including the resistor and blower motor. Products like ammonia, that might disinfect the air conditioning system of a vehicle, carry their own objectionable odors of long duration, that would be offensive to most vehicle owners.

The present invention preferably provides for the use of oxidants, and, preferentially, ozone, to solve the decontamination or asepsis problem. Ozone has a half life that has been measured from less than a minute to up to 12 minutes. Any odor associated with ozone would dissipate soon after its manufacture.

In its preferred embodiments, the present invention provides for a decontamination system for a motor vehicle comprising: a cockpit or passenger compartment; a sensor means for detecting oxidant levels located in the cockpit or passenger compartment; an HVAC unit having at least one heat exchanger element; an HVAC system comprising a the HVAC unit and an air distribution system including at least one duct for inputting air into and one duct for distributing air out of the HVAC unit; an oxidant generation means; and a controller means. In preferred embodiments of the present invention, the disposition of the HVAC unit allows exposure of the interior of the HVAC unit and the heat exchanger elements (e.g. the heater core and/or the evaporator) to a concentration of an oxidant at a level sufficient to be septicidal to micro-organisms. Also, preferably, at least one oxidant sensor means is present and is located in the cockpit, more preferably at a low level of the cockpit or passenger compartment.

In more preferred embodiments of the present invention, the decontamination system uses a feedback loop mechanism to assure the level of oxidant concentration within the cockpit or passenger compartment. This feedback loop mechanism, in the preferred embodiments of the present invention, is arranged to maintain an oxidant concentration in the cockpit or passenger compartment of between 0 to 0.06 ppm. In the preferred embodiments of the decontamination system of the present invention, the oxidant concentration of in the HVAC system is also controlled. Preferred is wherein the ozone concentration within the HVAC functional environment or system is maintained between 8 ppm and 1 ppm.

During the preferred processes of the present invention, the is maintained for a period of time wherein the effects are most efficient against microbial growth or development. In preferred embodiments of the present invention, the ozone concentration level is maintained in the HVAC system or the HVAC unit between about one hour and about six hours.

In a preferred method of the present invention, a good level of passenger comfort is achieved by: placing an ozone generator above the heat exchangers of a vehicle HVAC system; utilizing a vehicle controller to activate and time the ozone generator operation; and distributing ozone within the HVAC system by gravity feed.

Particularly preferred embodiments of the present invention provide for a decontamination system for controlling the effects of micro-organism contaminants in a vehicle HVAC functional environment comprising: a sensor; a controller; an HVAC unit having at least two heat exchanger elements; a vehicle owner/operator control switch; and an oxidant generator. In preferred embodiments, the oxidant produced by the oxidant generating means is directly introduced into the HVAC unit from the oxidant generating means. Also, in preferred embodiments, the controller means is a vehicle body controller. In more preferred embodiments, the decontamination system further comprising a timer, an ozone and vehicle sensor in a feedback loop mechanism wherein ozone generation is regulated or controlled by means of a series of actions involving the switch, ozone and vehicle sensors, a timer, and vehicle body controller, and wherein the heat exchanger elements of the HVAC unit are perfused or enveloped with ozone.

Preferably the amount of oxidant or preferably ozone, more preferably described as the oxidant or, more preferably, ozone concentration level employed in preferred embodiments of the present invention in the HVAC functional environment is between about 8 ppm and 0.045 ppm, more preferably between about 1.0 ppm and 0.045 ppm, even more preferably from about 0.1 to 0.045 ppm. Preferably, the ozone concentration level is maintained from one to eight hours, more preferably from about one to six hours, even more preferable from between about four to six hours during the decontamination period or cycle. Preferably, it is desirable to maintain an oxidant concentration in the cockpit or passenger compartment of less than 0.1 ppm, more preferably less than about 0.06 ppm, even more preferably between about 0 to 0.05 ppm during the decontamination period or cycle.

At preferable levels, the effectiveness of the decontamination is surprisingly increased, while at the same remaining within acceptable ozone level limits as determined by the EPA. The article "Ozone Monograph: Toxicity and Evaluation" by Robert Olcrest Ph.D CIH, CHCM, CSP, copyright 1990, which reports 0.5 PPM is well below the limit set by the EPA in 1978 as 120 parts per billion (equivalent to 235 micrograms/cubic meter of air) or a 0.12 PPM exposure for no more than one hour during any day of the year, exemplifies some of these necessary limitations.

In a further preferred method of the present invention, controlling an undesirable level of ozone in the passenger or cockpit area is also achieved by providing a sensor means, creating a feedback loop utilizing an ozone sensor which sends a signal via a controller means, and, in particular a 'vehicle controller', to the ozone generator or other control means; and modifying the delivery of the ozone to the HVAC unit in response to the signal from the sensor means.

Also preferred are embodiments wherein a vehicle owner/operator control means ('switch') is provided to allow the operator or occupant direct control of vehicle ignition (ignition switch) or oxidant generation (oxidant, or, particularly ozone generator switch). More preferred are embodiments wherein the feedback loop is controlled throughout the air treatment system via a vehicle body controller.

In preferred methods of the present invention, undesirable effects, such as odors and allergens produced by microorganisms or their products or bi-products are controlled or eliminated. At the level of the present invention, odors and other undesirable effects caused by other causes will also benefit from the effect of the ozone. In a more preferred of controlling odors and other undesirable effects due to microorganism contaminants in a vehicle HVAC system micro, the substances derived from micro-organism development or growth, are controlled via the use of an oxidant in the closed area of the HVAC system. In a particularly preferred method of controlling the undesirable effects of microorganism contamination in a motor vehicle, the undesirable effects are controlled by: providing oxidant into the HVAC unit via an oxidant generator; maintaining an oxidant concentration of between 0.45 ppm and 0.1 ppm in the HVAC unit during a period of from about 4 hours to 6 hours in the HVAC unit; maintaining an oxidant concentration of less or equal to about 0.1 ppm at all times in the cockpit or passenger compartment of a vehicle; providing for a drain in the HVAC unit for removing oxidant or condensate during provision of oxidant into the HVAC unit; purging the HVAC, if necessary, to remove excess oxidant, and, thereby; reducing the amount of odor and allergen that reaches the cockpit or passenger compartment of a vehicle. Preferred are methods wherein the oxidant concentration in the cockpit or passenger compartment is maintained at less than or equal to about 0.05 ppm. Also preferred is where the contaminant originators to be controlled (the cause of the undesired effects) are selected from the group consisting of bacteria, yeast, fungi, mold and related allergens. Even more preferred is wherein the contaminant originators to be controlled are bacteria and yeast. In most preferred methods, the concentrations of ozone within the cockpit or passenger compartment of a vehicle is controlled by a feedback mechanism.

In an even more preferred method, the distribution of the ozone within the HVAC system is done by gravity feed.

Figure 2:
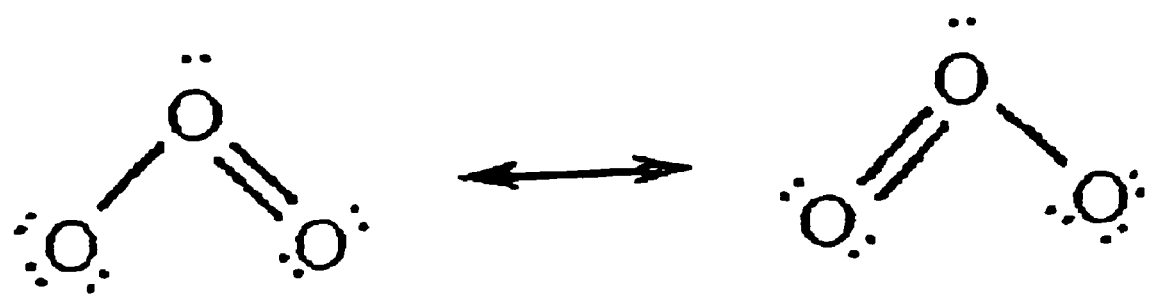
FIG. 2 is a representation of an oxidant, in particular, ozone, in accordance with an aspect of the present invention.

In FIG. 1, an HVAC apparatus, in accordance with an aspect of the present invention is disclosed. An ozone generation system comprising the HVAC system, ozone generator and sensor means and control means, is preferably provided. In FIG. 2, molecular oxygen that has been converted to its second allotrope (ozone) in the presence of electric discharge is described:

O=O-O

An ozone generator (1) is mounted to HVAC unit (2), above evaporator (3) and heater core (4), in the air path (5), downstream from blower wheel (6), above or before temperature door (7), and mode door (8). The ozone generator is electrically wired (9), to the vehicle body controller (10). The vehicle body controller is electrically wired to the control (ignition switch) (11), blower motor (12), passenger compartment ozone sensor (13), occupant 'ozone generator mode' or ozone generator switch (14), door ajar sensor (15), and vehicle battery (16), climate control head (17), and timer function (18).

Figure 3:
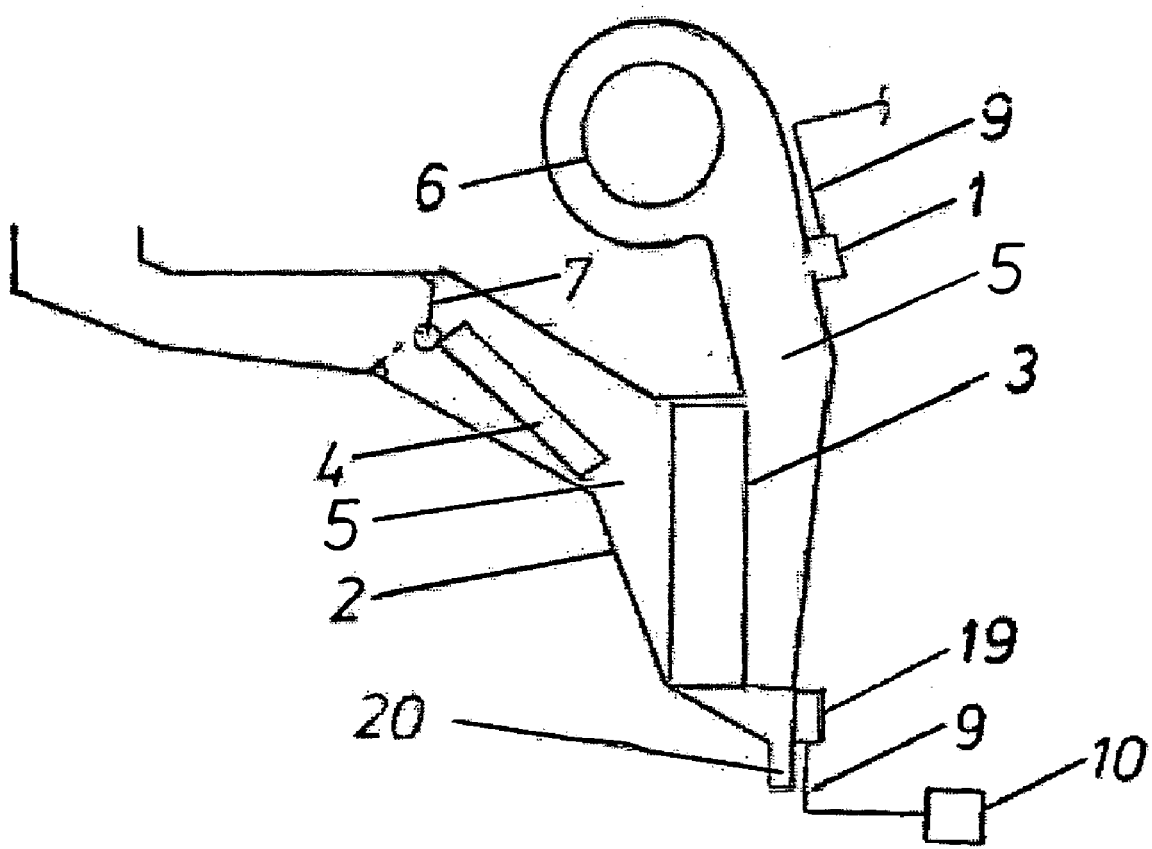
FIG. 3 is an additional view of the HVAC unit, with condensate drain and an operative drain tube plug, in accordance with an aspect of the present invention.

Referring to FIG. 3 is illustrated another view of a preferred embodiment of the present invention of an air treatment system comprising an HVAC functional environment with HVAC architecture as shown. Ozone generator is mounted to HVAC unit (2), above evaporator (3) and heater core (4), in the air path (5), downstream from blower wheel (6), above or before temperature door (7), and mode door (8). The ozone generator is electrically wired (9), to the vehicle body controller (10).

In addition, drain tube (20) and operative drain tube plug (19) is provided, with drain tube plug (19) initiated by the vehicle controller (10) by means such as wiring (9) or other means such as, but not limited, pneumatic hose or hoses, push-pull cable or cables, and electric actuation or a hydraulic system. Drain tube plug (19) prevents prevent ozone from migrating out of the HVAC unit (2) by way of drain tube (20) while ozone generator (1) is in operation. Drain tube plug (19) will be in the open position for normal HVAC operation (without ozone perfusion) as needed.

Figure 4A:
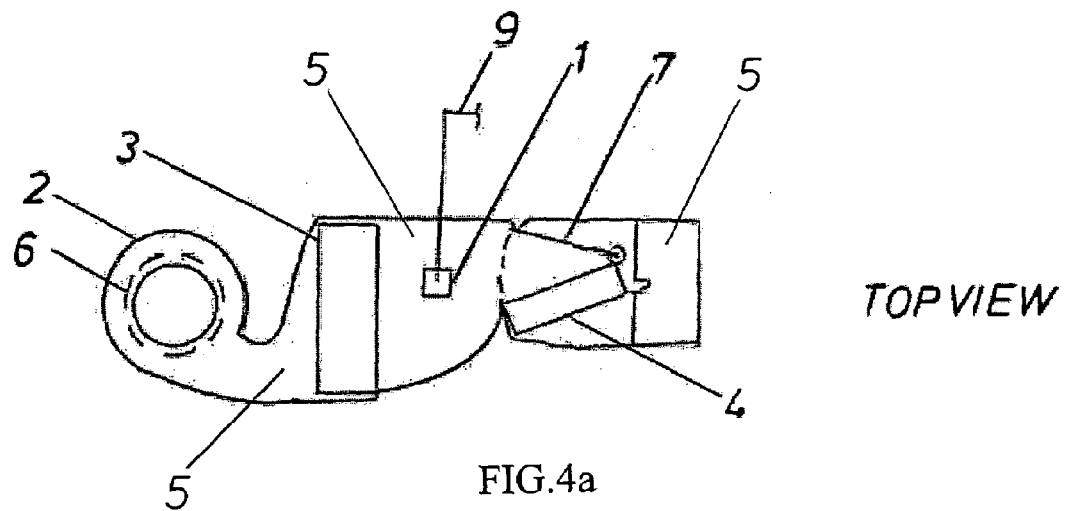
FIGS. 4a and 4b are top view and front view, respectively of an HVAC unit with lateral architecture and ozone generator above the heat exchangers (heater core and evaporator), in accordance with an aspect of the present invention.
Figure 4B:
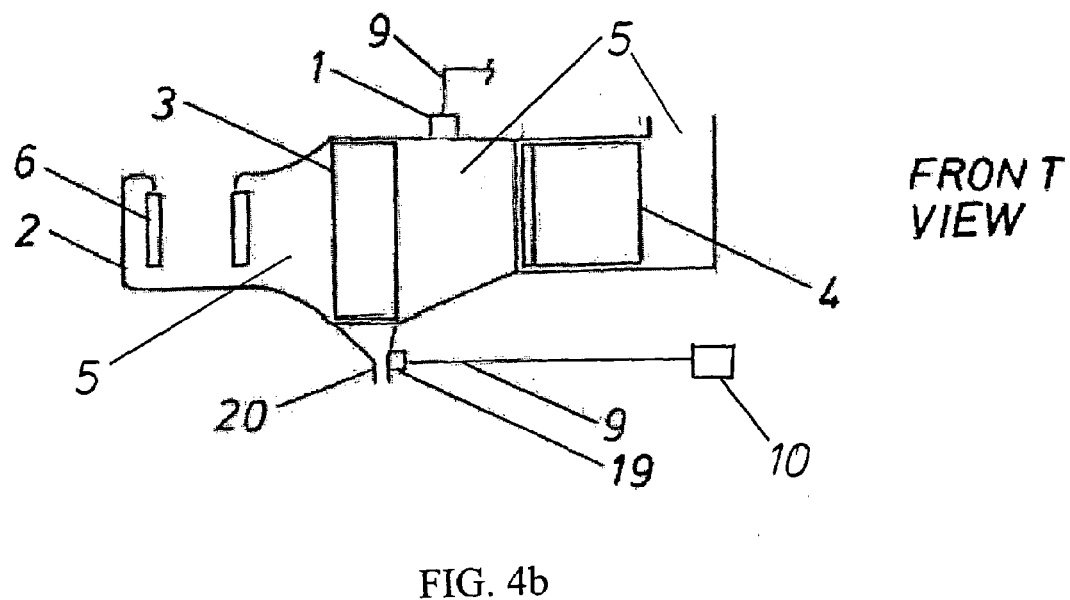

Referring to FIGS. 4a and 4b is illustrated an HVAC functional environment of a lateral HVAC architecture from a top and front view. An ozone generator (1) is mounted to HVAC unit (2), above evaporator (3) and heater core (4), in the air path (5), downstream from blower wheel (6), above or before temperature door (7), and mode door (8). The ozone generator is electrically wired (9), to the vehicle body controller (10). In this embodiment, ozone generator (1) is positioned or located above the heat exchangers (3) and (4) and in communication with the vehicle body controller (10) by means of wiring (9). Ozone generator (1), though located above the heat exchangers (3) and (4), is not limited to any particular orientation in that area above the heat exchangers. In additional, drain tube (20) and drain tube plug (19) is provided, with drain tube plug (19) initiated by the vehicle controller (10)

Figure 5A:
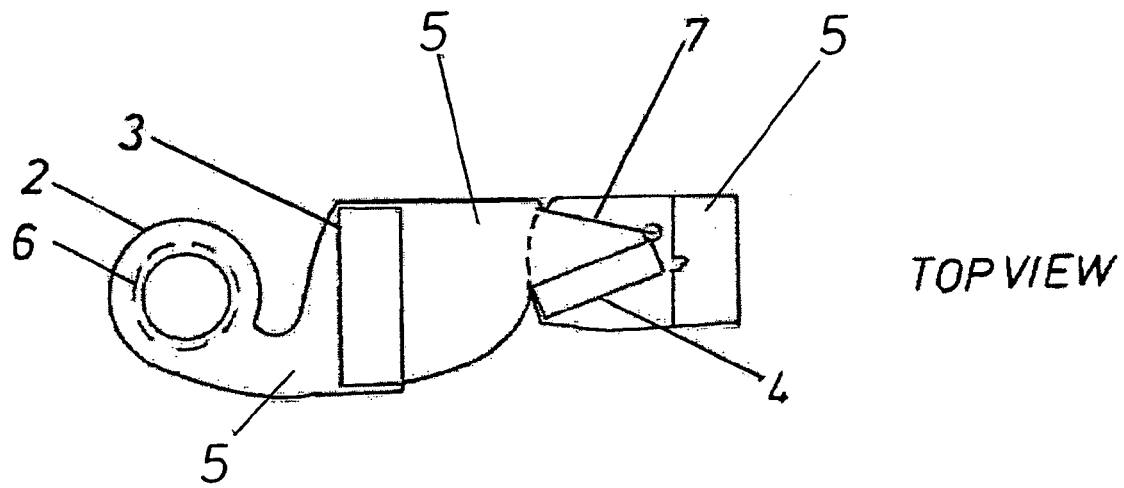
FIGS. 5a and 5b are top and front views respectively of an HVAC unit with oxidant or ozone generator placed other than above the heat exchangers and having a fan for circulating oxidant, in accordance with an aspect of the present invention.
Figure 5B:
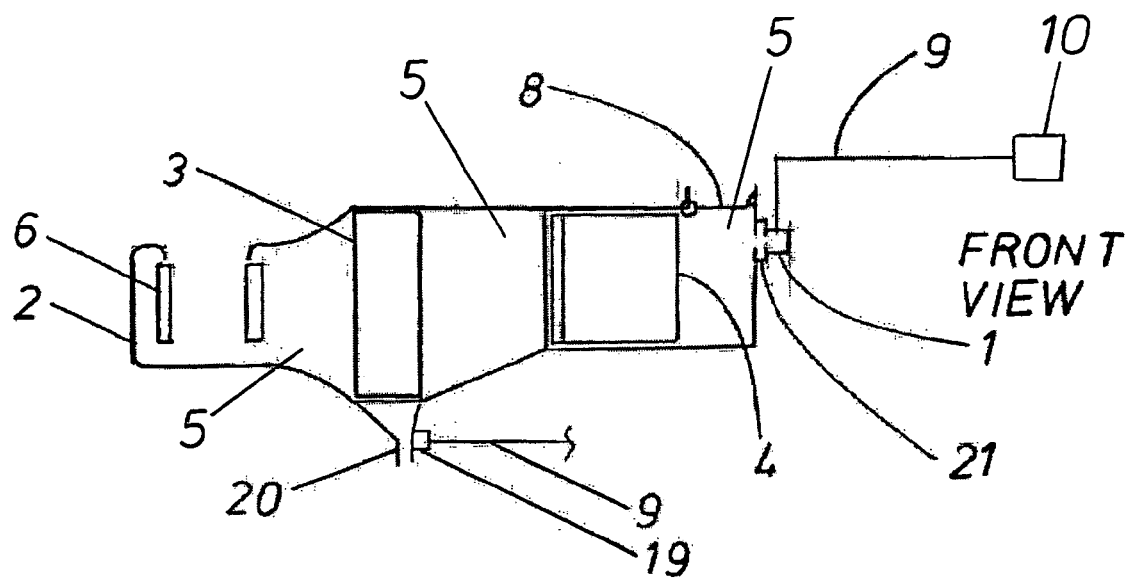

Referring to FIGS. 5a and 5b is illustrated an HVAC functional environment of a system in which ozone generator (1) is not located above the heat exchangers (3) and (4) to provide the oxidizing function by means of gravity feed. In this embodiment, due to the fact that an alternate location is used, a propulsion means, such as a fan (21) is used. Oxidant generator (1) on the side of HVAC unit (2), with a fan (21) circulates oxidant within the HVAC unit. Oxidant generator (1) may be located in any position or orientation, in this embodiment of the design. In additional, drain tube (20) and drain tube plug (19) is provided, with drain tube plug (19).

Figure 6:
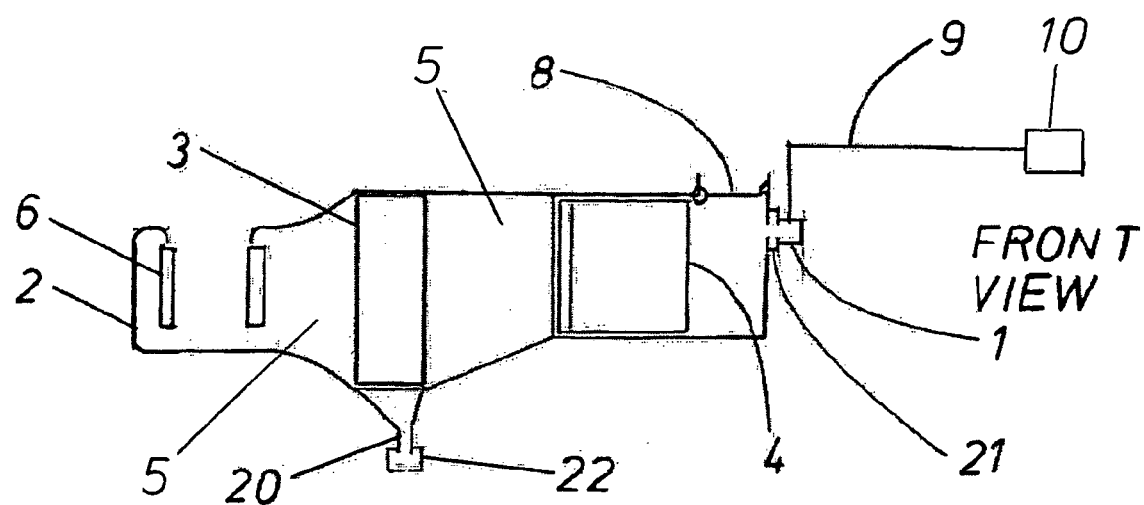
FIG. 6 is a front view of an HVAC unit in accordance with an aspect of the present invention, having mechanical drain plug to control the rate of oxidant from the drain tube opening.

FIG. 6, shows a front view of an HVAC functional environment in accordance with the present invention having mechanical drain plug (22) to control the rate of flow of oxidant from drain tube opening. The drain plug can be but is not limited to a compression molded rubber cap with a slit opening (22), that remains closed until it is opened by the weight of condensate that is produced by evaporator (3). The oxidant is produced by generator (1) at a rate that is greater than any oxidant leakage that may occur through the mechanical drain plug (22).

In a preferred embodiment of the present invention, the HVAC unit ozone generator's operation may be directly managed by the vehicle owner/operator or other occupant by placing the generator in one of three operating modes: off; manual; or automatic.

The ozone generator switch (14) is accessible to the vehicle owner/operator or other occupant as a function in the cockpit or passenger compartment preferably on the instrument panel or by other means such as remote lock/unlock switch, keyless entry switch, and glove box switch. When in the "off" mode the vehicle body controller (10) will not activate the timer (18) or other system functions. The location of the switch 14 may be anywhere in the passenger cabin, but preferably on the instrument panel within reach of an occupant sitting in the driver's seat.

When in "manual" mode the body controller (10) operates the ozone generation system according to the following parameters:
- the system will not operate if the door ajar sensor (15) is activated;
- if functioning the system will be deactivated if the door ajar sensor (15) is activated;
- the system will not operate if the key is in the ignition (11); and
- the system will not operate if the ozone sensor (13) detects an unacceptable level of ozone in the vehicle interior. The sensitivity of the sensor is preset according to the laws, regulations, or other parameters specific to where the vehicle was purchased or other rationale.

When operating for exemplary purposes, the generator is set, the body controller (10) initiates the timer (18) to operate the ozone generator (1) for a fixed period, preferably from about one to six hours, more preferably from about four to six hours, most preferably for about four hours, depending on the concentration of oxidant provided in the 'closed' HVAC unit for one four hour cycle. The body controller will not initiate the process again until the manual switch is reset by the owner/operator or other occupant.

When in automatic mode the system function remains the same during the, for example, four hour cycle time as described above (same in the manual mode, with the limitations as described above). During the activation period (four hour cycle) the interior of the HVAC unit is provided with enough ozone to more or less completely permeate the heat exchangers and interior of the HVAC unit. If any internal door or doors block access to one of the exchangers the control head (17) will be initiated to move the door (7) or (8) to a favorable position. The control head (17) will also be initiated by the body controller (10) to close the floor discharge opening.

Figure 7:
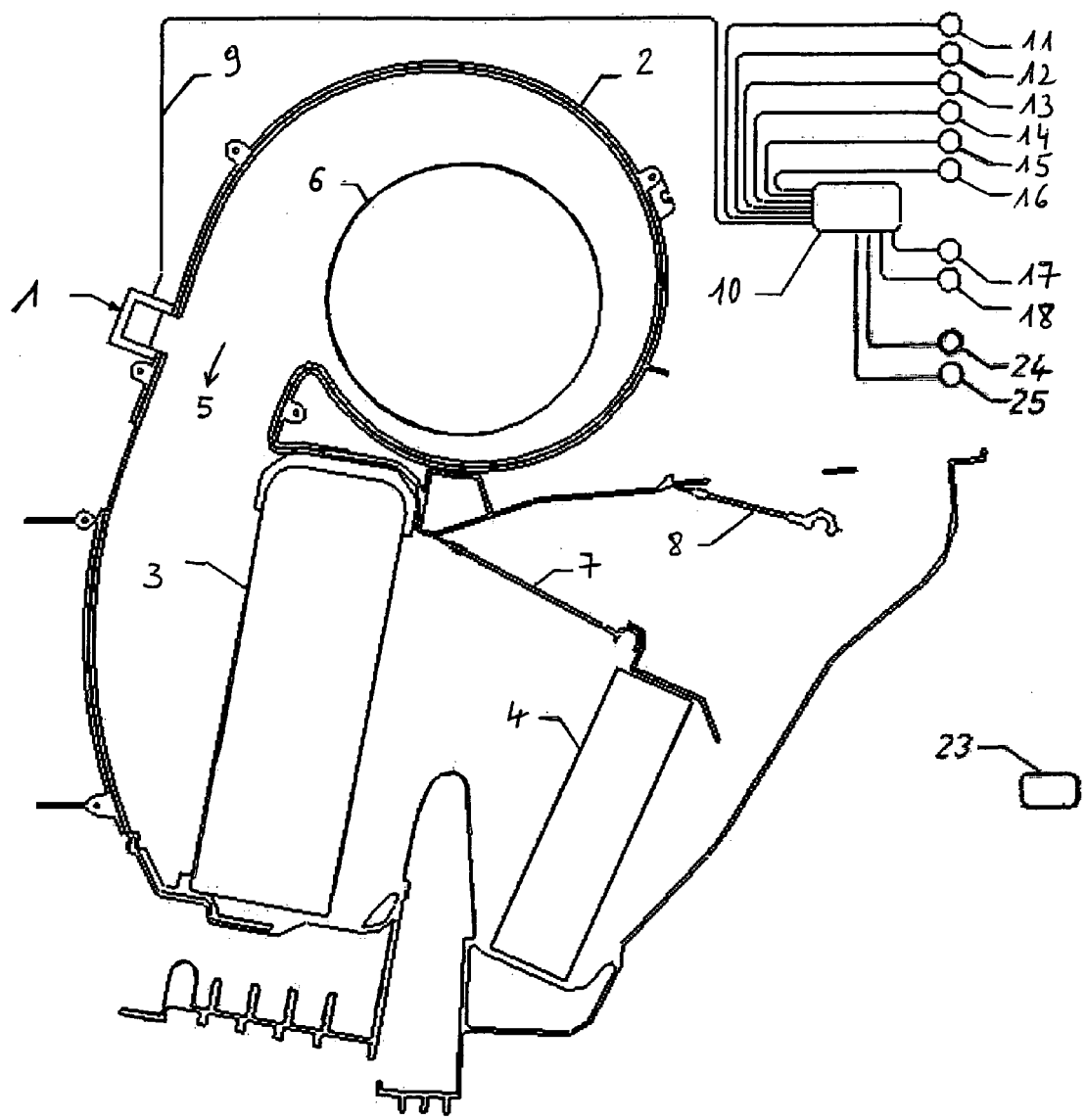
FIG. 7 is an elevational cross section view of an HVAC unit in accordance with an aspect of the present invention.

Referring to FIG. 7 the vehicle owner/operator initiates the oxidation sequence by remote transmitter (23), An initiation signal is received by the signal receiver (25) and relayed to the body controller (10). All sensors checked are made including, but not limited to, the door ajar sensor (15), and seat occupant sensor (24), ignition (11) and timer. The control logic initiates the oxidation sequence when the sensors indicate the vehicle is unoccupied and not running.

Figure 8A:
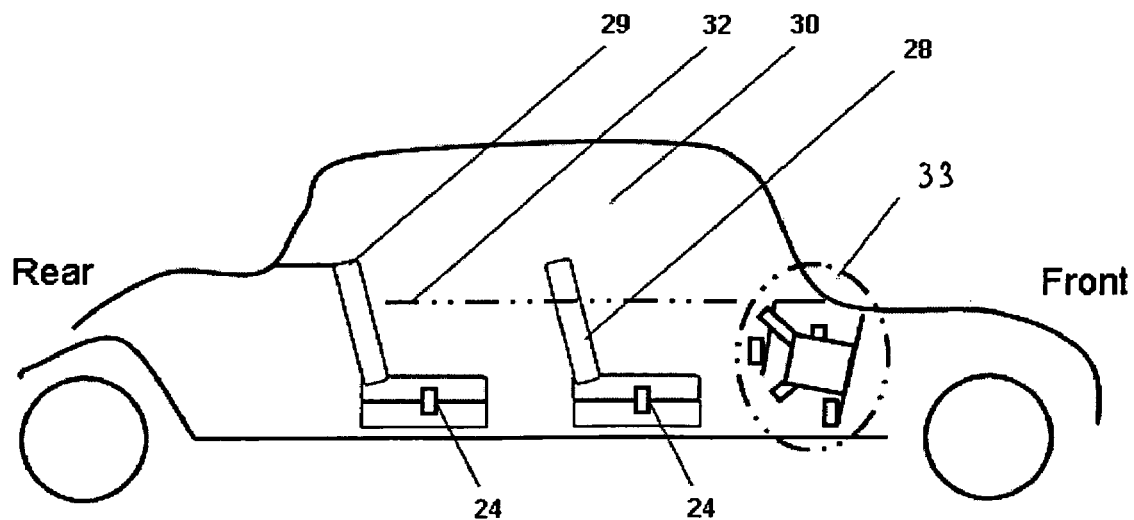
FIG. 8 is a schematic view of a decontamination system in accordance with an aspect of the present invention.
Figure 8B:
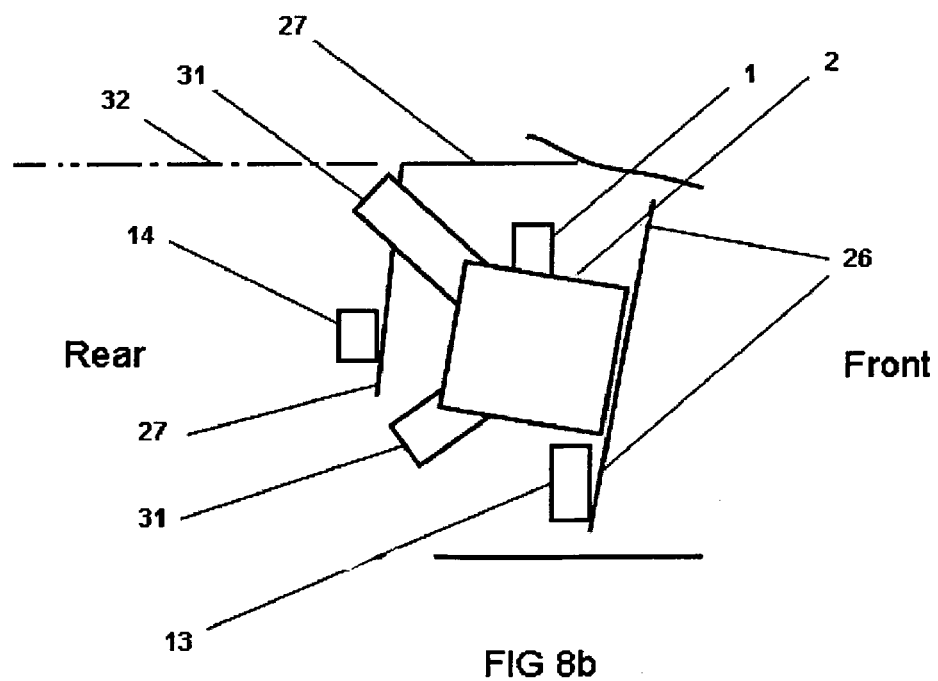

Referring to FIGS. 8a and 8b the horizontal midline (32) is graphically described as a horizontal plane even with the upper surface of the instrument panel (27). The oxidant sensor (13) is located within the passenger cabin interior (30), below the horizontal midline (32) and preferably below the HVAC Unit (2) against the bulkhead (26). Preferred embodiments are also shown with oxidant sensor (13) placed below the horizontal midline (32), and under the front seat (28) or under the rear seat (29). Seat occupant sensors (24) are in communication with the body controller (10) to detect the presence of a person or animal on the seats.

Several micro-organisms may be controlled in preferred aspects of the present invention, particularly where low concentration levels or short exposure times to ozone as oxidant are provided. Particularly susceptible micro-organisms include bacteria and yeast.

In other embodiment of this invention, oxidant levels are controlled by adjusting the sensitivity of sensor (13). The adjustment mechanism is incorporated into the ozone generator switch (14) providing the vehicle owner, operator with the range of adjustment from but not limited to 0.1 ppm to continuous oxidant production in the unoccupied vehicle.

Several embodiments of the present invention could be developed from the basic types of HVAC architecture. In preferred embodiments of the present invention where gravity feed cannot be utilized to completely disinfect the HVAC system, a combination of gravity feed and system ventilation can be used to perfuse the HVAC unit and associated ducts. In preferred embodiments, the ozone generator may be attached to the air inlet housing of the HVAC system to improve the circulation of the ozone; preferably control of the blower related thereto leads to better air mixing, and, thus, more efficient use of ozone, in these preferred embodiments.

What is claimed is:

1. A method of controlling the undesirable effects of micro-organism contamination in a motor vehicle by:
   providing oxidant into the HVAC unit via an oxidant generator;
   maintaining an oxidant concentration of between 0.45 ppm and 0.1 ppm in the HVAC unit during a period of from about 4 hours to 6 hours in the HVAC unit;
   maintaining an oxidant concentration of less or equal to about 0.1 ppm at all times in the cockpit or passenger compartment of a vehicle;
   providing for a drain in the HVAC unit for removing oxidant or condensate during provision of oxidant into the HVAC unit;
   purging the HVAC, if necessary, to remove excess oxidant;
   shutting off the provision of oxidant into the HVAC unit or the cockpit or passenger compartment of the vehicle if the oxidant concentration exceeds 0.1 ppm in either the HVAC unit or cockpit or passenger compartment of the vehicle;
   thereby reducing the amount of odor and allergen that reaches the cockpit or passenger compartment of a vehicle.

2. A method as in claim 1 wherein the oxidant concentration in the cockpit or passenger compartment is maintained at less than or equal to about 0.05 ppm.

3. A method as in claim 1 wherein the oxidant is ozone and the contaminant originators to be controlled are selected from the group consisting of bacteria, yeast, fungi, mold and related allergens.

4. A method as in claim 3 wherein the contaminant originators to be controlled are bacteria and yeast.

5. A method as in claim 4 whereby the concentrations of ozone within the cockpit or passenger compartment of a vehicle is controlled by a feedback mechanism.

* * * * *